United States Patent
Brajnovic

(10) Patent No.: US 7,866,981 B2
(45) Date of Patent: Jan. 11, 2011

(54) IMPLANT ARRANGEMENT

(75) Inventor: Izidor Brajnovic, Gothenburg (SE)

(73) Assignee: Nobel Biocare Services AG, Zurich-Flughafen (CH)

( * ) Notice: Subject to any disclaimer, the term of this patent is extended or adjusted under 35 U.S.C. 154(b) by 440 days.

(21) Appl. No.: 11/916,257

(22) PCT Filed: Apr. 27, 2006

(86) PCT No.: PCT/SE2006/000493

§ 371 (c)(1),
(2), (4) Date: Nov. 30, 2007

(87) PCT Pub. No.: WO2006/130064

PCT Pub. Date: Dec. 7, 2006

(65) Prior Publication Data

US 2009/0317763 A1    Dec. 24, 2009

(30) Foreign Application Priority Data

Jun. 3, 2005    (SE)    .................................... 0501286

(51) Int. Cl.
    *A61C 8/00*    (2006.01)
(52) U.S. Cl. ...................... 433/173; 433/174
(58) Field of Classification Search .................. 433/173, 433/174
    See application file for complete search history.

(56) References Cited

U.S. PATENT DOCUMENTS

| | | | | |
|---|---|---|---|---|
| 4,934,935 A | | 6/1990 | Edwards | |
| 4,993,950 A | * | 2/1991 | Mensor, Jr. | 433/173 |
| 5,022,860 A | * | 6/1991 | Lazzara et al. | 433/174 |
| 5,362,235 A | * | 11/1994 | Daftary | 433/172 |
| 5,362,236 A | * | 11/1994 | Branemark | 433/173 |
| 5,564,926 A | * | 10/1996 | Branemark | 433/174 |
| 6,048,203 A | | 4/2000 | Rosenberg | |
| 6,280,194 B1 | | 8/2001 | Björn et al. | |

FOREIGN PATENT DOCUMENTS

| | | |
|---|---|---|
| EP | 0583829 A1 | 2/1994 |
| EP | 0599794 A2 | 6/1994 |
| EP | 0823243 A2 | 2/1998 |

OTHER PUBLICATIONS

International Search Report received in corresponding PCT Application No. PCT/SE2006/000493, mailed Aug. 3, 2006.

* cited by examiner

*Primary Examiner*—Ralph A Lewis
(74) *Attorney, Agent, or Firm*—Knobbe Martens Olson & Bear, LLP

(57) ABSTRACT

An anchoring arrangement is provided for anchoring a dental prosthesis to a patient. The arrangement can comprise an implant, a sleeve, and a fastening screw. The implant can comprise a coronal portion and an apical portion. The apical portion can be configured to extend from within a jaw bone and into a zygoma. The coronal portion can include a substantially planar surface extending transversely relative to a longitudinal axis of the apical portion and a threaded aperture. The threaded aperture can extend from the substantially planar surface into the implant transversely relative to the longitudinal axis of the apical end of the implant. The sleeve can comprise an end portion configured to mate with the substantially planar surface of the implant. The fastening screw can be disposed through the sleeve and fastened to the threaded aperture.

29 Claims, 2 Drawing Sheets

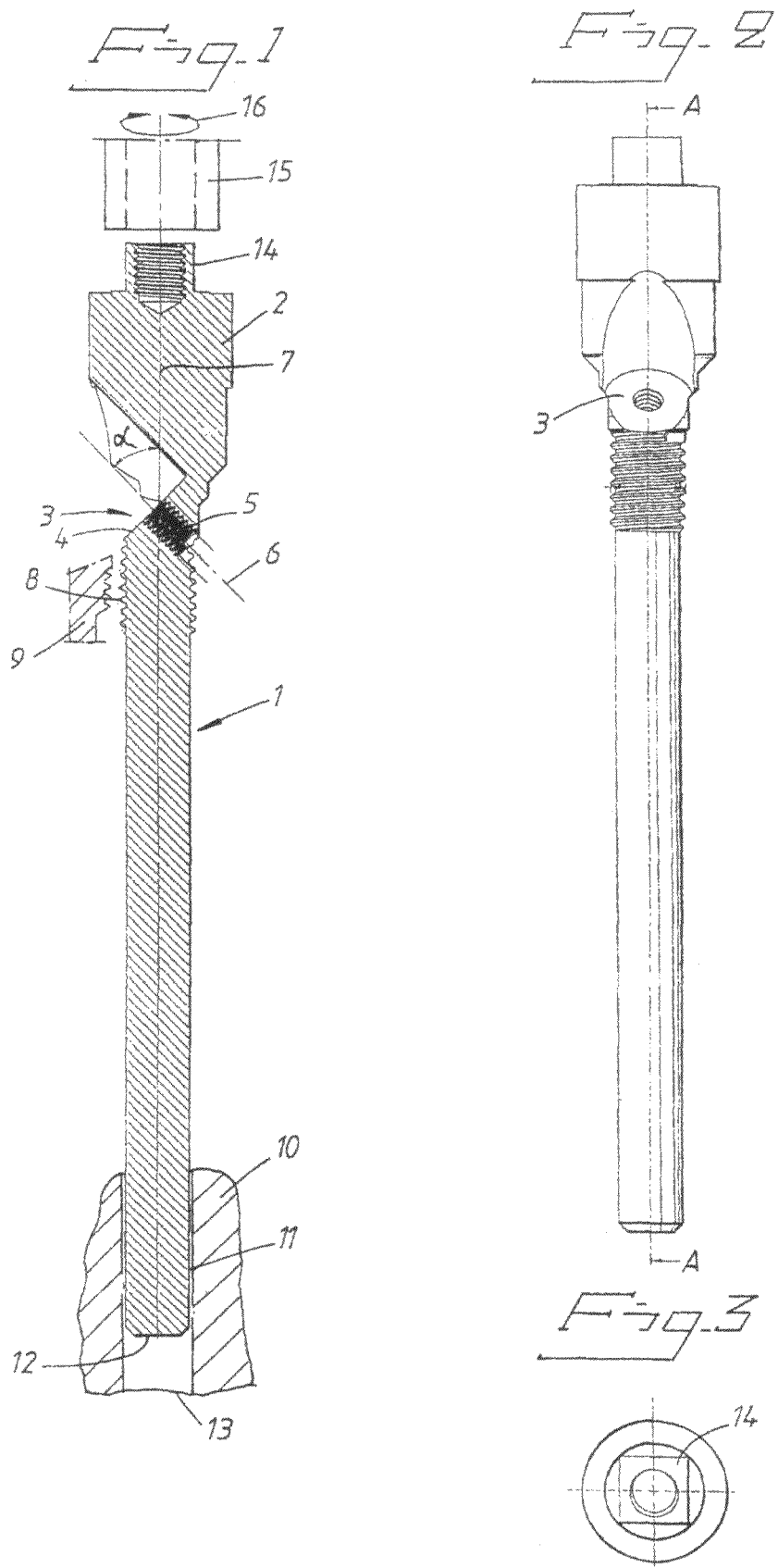

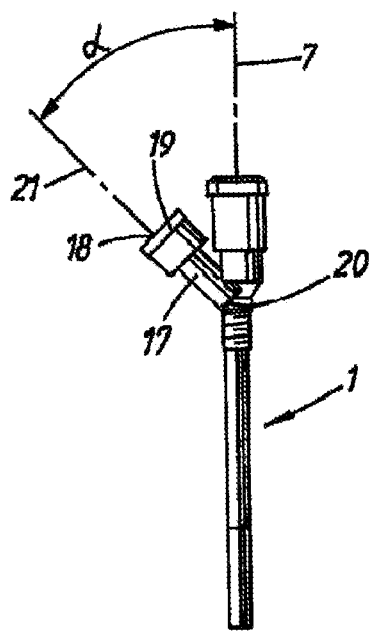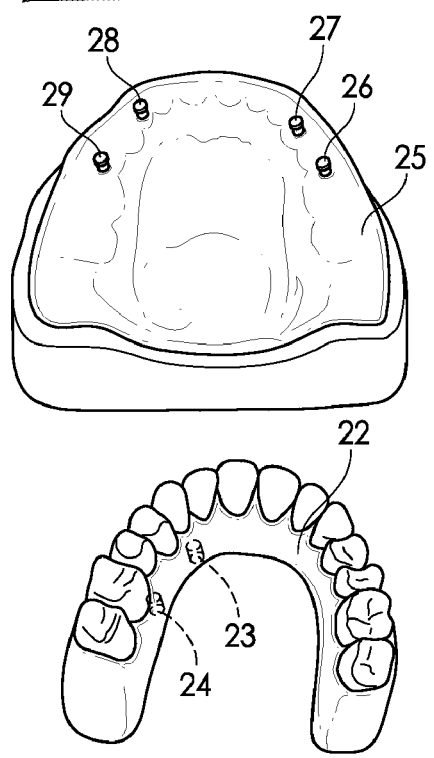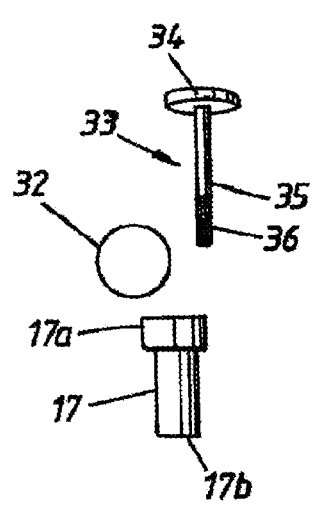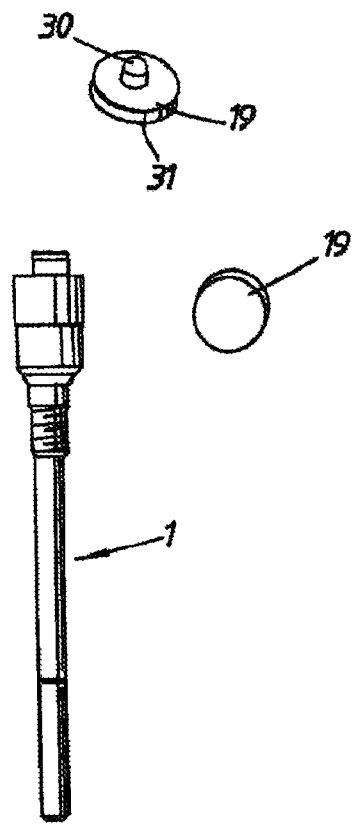

IMPLANT ARRANGEMENT

PRIORITY INFORMATION

This application is a U.S. National Phase of International Application No. PCT/SE2006/000493, filed Apr. 27, 2006, which claims priority to Swedish Patent Application No. SE 0501286-9, filed Jun. 3, 2005, each of which is hereby incorporated by reference in its entirety.

BACKGROUND

1. Field of the Invention

The present invention relates to an implant arrangement which extends in a hole formed between a tooth fixture and the zygoma. The longitudinal axis of the implant extends at an angle in relation to a longitudinal direction for a fastening screw, by means of which the fixture can be anchored to the implant.

2. Description of the Related Art

In general, partially or completely edentolous upper jaws can be treated by drilling holes in the jawbone and the consequent insertion of anchoring elements in these holes by the use of preferably cylindrical fixtures with an outer thread and to supply them with single-tooth or bridge prostheses in the latter case with more than one fixture to be applied in the bone in order to retain a bridge construction.

In certain cases when the patient has been edentolous for a long time and for this reason the jawbone has been partly resorbed, the dimension and the retention force of the jawbone is inadequate for the anchoring of one or several fixtures. The patient may thus not be successfully treated with a desirable prosthetic appliance, or may not be willing to accept the risk which in such a case may be considerable, for loosing the prosthesis or a fractured jawbone. Thus, certain implants have been developed to aid in anchoring prosthetic appliances in such cases, and reference may be made inter alia to U.S. Pat. Nos. 5,362,236 and 6,280,194, the entireties of the disclosures of which are incorporated by reference herein.

SUMMARY OF THE INVENTION

In accordance with an embodiment disclosed herein is the realization that in tooth prosthesis fixtures, there is a need to ensure an appropriate fixture which has points of connection situated at the best possible sites in the mouth. The fixture must not have any tendency to accumulate bacteria and contaminants and must additionally have positions that are advantageous for the patient. Preferably, known techniques can be used for the fixture, and, at the same time, clear and simple components can be used.

In an embodiment, a tooth fixture is provided that consists of a tooth prosthesis whose receiving opening for the fastening screw can be located on the inside of the tooth prosthesis. In its position when screwed into the zygoma, the implant can be rotatable for orienting a receiving part for said fastening screw at said opening. The fastening screw can be screwed into a corresponding thread in the receiving part. The fastening screw can be fastened via a surrounding sleeve which, at its first end, bears against the receiving part and, at its second end, supports a cap-shaped part with which the head of the fastening screw can be covered.

In further embodiments, the sleeve is designed with an end surface by means of which the sleeve bears against a top surface of the receiving part across its full extent. At its end extending away from the receiving part, the sleeve carries a cap-shaped part, by means of which the screw arrangement can be sealed off.

In accordance with embodiments disclosed herein, known implants can be used while ensuring that the anchoring function in performed in a safe and reliable manner and preventing the accumulation of contaminants and bacteria. The implant can be of the type that comprises one or more threads of the same or different diameters. The implant can be applied in threaded and/or unthreaded holes which can be formed in accordance with what is set out in an application submitted on the same day as the present patent application and filed by the same applicant.

BRIEF DESCRIPTION OF THE DRAWINGS

The abovementioned and other features of the inventions disclosed herein are described below with reference to the drawings of the preferred embodiments. The illustrated embodiments are intended to illustrate, but not to limit the inventions. The drawings contain the following figures:

FIG. 1 is a cross-sectional side view of an implant, according to an embodiment.

FIG. 2 is a side view of the implant shown in FIG. 1 wherein the implant is turned through 90° about its longitudinal axis.

FIG. 3 is a top end view of a tightening member arranged at an upper end of the implant of FIGS. 1-2, according to an embodiment.

FIG. 4 is a side view of the implant of FIG. 1 including a connector arrangement by means of which a tooth prosthesis can be connected to the implant, according to an embodiment.

FIG. 5 is a perspective view of a tooth prosthesis and a unit which indicates the main directions of the implants, according to an embodiment.

FIG. 6 includes side views of the implant with associated screwing arrangements for a tooth prosthesis, according to another embodiment.

DETAILED DESCRIPTION OF THE PREFERRED EMBODIMENTS

In FIG. 1, an implant is designated by 1. At its upper parts, the implant has an implant head 2 and a receiving part for an anchoring screw, which is indicated symbolically by 3. The receiving part has a plane top surface 4, which is circular in the illustrative embodiment. Extending centrally within said surface there is a threaded hole 5 with a longitudinal axis 6 which is angled in relation to the longitudinal axis 7 of the implant by an angle $\alpha$. Said angle can assume values of between 30-60° and is preferably ca. 45°.

At its parts under said receiving part 3, the implant 1 has a thread 8 via which the implant can be screwed into a jaw bone which is indicated symbolically by 9 and which can be threaded in advance or can be tapped by means of the thread 8 shown. The lower parts of the implant are threadless and can be anchored in the zygoma, which is designated symbolically by 10. The hole 11 formed in the zygoma 10 can be a through-hole, and the implant 1 can extend to a position 12 before the exit 13 of the hole. At its upper end, the implant is also provided with an actuating member 14 for a tool 15 which can be of a type known per se. The actuating member 14 can be a polygonal part, for example a quadrangular part, via which the tool 15 cooperates with the implant for turning the latter about the longitudinal axis 7 in directions of rotation 16.

FIG. 2 shows the implant turned through 90° about the longitudinal axis in relation to FIG. 1. FIG. 2 shows, among other things, the configuration of said surface 3.

FIG. 3 shows the section of the actuating member 14 in the transverse direction of the implant.

FIG. 4 shows the implant 1 according to FIGS. 1 and 2 and an anchoring arrangement for anchoring a tooth prosthesis to the implant. The anchoring arrangement comprises a sleeve 17 which, at one end 18, is provided with a cap-shaped part 19 and which, at its other end 20, bears with a plane end surface against said receiving surface 3 (see FIG. 2, inter alia). Located inside the sleeve 17, and covered by the cap-shaped part 19, there is a fastening screw which is described in more detail below and which can be screwed into the thread 5 (see FIG. 1). The longitudinal axis 21 of the arrangement and the longitudinal axis 7 of the implant are angled relative to one another by said angle α.

In FIG. 5, reference number 22 designates a tooth prosthesis which is to be fastened to a number of implants, which number can be four. Receiving openings in the tooth prosthesis are designated by 23 and 24 in FIG. 5. With the aid of a unit 5 are shown the applications for four implants according to FIG. 4. The implants are shown from above by 26, 27, 28 and 29.

As will be seen from FIG. 5, the main directions of the implants 26-29 are different than the main directions of the openings 23 and 24. The connector arrangement for the tooth prosthesis thus comprises said sleeve 17 which, at one end, has a widened part 17a and, at its other end, has said end surface 17b which bears against the receiving surface 3 (see FIG. 1).

The cap-shaped part 19 is shown in two views, one from above and one from underneath. The cap-shaped part has a knob 30 on its top face and has a flat part and, extending down from this, an edge 31.

The sleeve-shaped part 17 has an inner shoulder surface (not shown) which carries a sealing member 32. The arrangement also includes a fastening screw 33 with a disk-shaped top part 34 and a pin-shaped part 35 which is provided with a thread 36 at the free end of the screw.

By means of said thread 36, the screw can be screwed into the thread 5 in FIG. 1, which thus constitutes a corresponding thread. The disk-shaped part reaches an end position at the aforementioned inner shoulder surface of the sleeve 17 and the sealing member 32 lies between the disk-shaped part 34 and the inner shoulder in the sleeve 17. Once the seal and the screw have been introduced into the sleeve 17 and this, together with the screw, has been brought to lie against the implant in accordance with FIG. 4, the cap-shaped part 19 can be applied to the widened part of the sleeve and an effective seal is obtained in this way at the point of connection. The end surface 17b bears against the receiving surface across its full extent.

Although these inventions have been disclosed in the context of certain preferred embodiments and examples, it will be understood by those skilled in the art that the present inventions extend beyond the specifically disclosed embodiments to other alternative embodiments and/or uses of the inventions and obvious modifications and equivalents thereof. In addition, while several variations of the inventions have been shown and described in detail, other modifications, which are within the scope of these inventions, will be readily apparent to those of skill in the art based upon this disclosure. It is also contemplated that various combination or sub-combinations of the specific features and aspects of the embodiments may be made and still fall within the scope of the inventions. It should be understood that various features and aspects of the disclosed embodiments can be combined with or substituted for one another in order to form varying modes of the disclosed inventions. Thus, it is intended that the scope of at least some of the present inventions herein disclosed should not be limited by the particular disclosed embodiments described above.

The invention claimed is:

1. An anchoring arrangement for anchoring a dental prosthesis to a patient, the arrangement comprising:
   an implant comprising a coronal portion and an apical portion that defines a longitudinal axis, the apical portion configured to extend from within a jaw bone and into a zygoma, the coronal portion including a head and a receiving part disposed between the head and the apical portion, the head comprising an engageable structure for rotating the implant, the receiving part comprising a substantially planar surface extending transversely relative to the longitudinal axis of the apical portion and a threaded aperture extending from the substantially planar surface into the implant, the threaded aperture extending transversely relative to the longitudinal axis of the apical end of the implant;
   a sleeve comprising a widened portion disposed at a coronal end thereof and an end portion disposed at an apical end thereof, the end portion being configured to mate with the substantially planar surface of the implant; and
   a fastening screw that can be disposed through the sleeve and fastened to the threaded aperture.

2. The arrangement of claim 1, further comprising a cap which is supported within the sleeve to cover the fastening screw.

3. The arrangement of claim 2, further comprising a sealing member configured to lie between a head of the fastening screw and an interior surface of the sleeve.

4. The arrangement of claim 1, wherein the apical portion of the implant includes an apical threadless section and a coronal threaded section.

5. The arrangement of claim 4, wherein the coronal threaded section is configured to lie within the jawbone and the apical threadless section is configured to be received within a hole formed in a zygoma of the patient.

6. The arrangement of claim 1, wherein the head comprises a threaded aperture.

7. The arrangement of claim 1, wherein the planar surface of the receiving part traverses the longitudinal axis of the apical end of the implant.

8. The arrangement of claim 7, wherein the head comprises a threaded aperture that is coaxially aligned with the longitudinal axis of the implant.

9. The arrangement of claim 1, wherein the engageable structure of the head comprises an actuating member, the actuating member being configured to be engaged by a screwing tool for rotating the implant relative to the patient.

10. The arrangement of claim 9, wherein the actuating member extends upwardly from the head of the implant.

11. The arrangement of claim 9, wherein the actuating member comprises at least one flat surface.

12. The arrangement of claim 9, wherein the actuating member comprises a polygonal part extending upwardly from the implant.

13. An anchoring implant arrangement for anchoring a tooth prosthesis to a dental implant, the arrangement comprising:
   a fastening screw;
   an implant comprising an implant body, the implant body defining a longitudinal axis and a threaded section, the threaded section configured to secure the implant to a jaw bone of a patient, the implant further comprising a head and a receiving part disposed between the head and the threaded section, the head comprising an engageable structure for rotating the implant, the receiving part comprising a surface extending transversely relative to the longitudinal axis of the implant, the receiving part further comprising a threaded aperture extending from the surface for receiving the fastening screw therein; and a sleeve comprising a widened portion disposed at a coronal end thereof and an end portion disposed at an apical end thereof, the end portion being configured to mate with the surface of the receiving part of the implant, the sleeve being configured with the fastening screw being passable therethrough to extend toward the threaded aperture of the receiving part;

wherein the longitudinal axis of the implant extends at an angle relative to a longitudinal axis of the fastening screw when the fastening screw is attached to the receiving part for anchoring the dental prosthesis to the implant.

14. The arrangement of claim 13, wherein the implant includes an apical threadless section beyond the threaded section thereof, the threadless section configured to be received within a hole formed in a zygoma of the patient.

15. The arrangement of claim 13, further comprising a cap-shaped part configured to fit within the widened portion of the sleeve to cover a head of the fastening screw.

16. The arrangement of claim 15, wherein the cap-shaped part has a planar top surface and an edge extending down from the planar top surface, the edge being configured to cooperate with an inner surface of the sleeve at the coronal end.

17. The arrangement of claim 16, wherein the widened portion of the sleeve comprises an inner shoulder surface configured to receive a sealing member, the sealing member and the edge of the cap-shaped part being cooperative to form a seal when the fastening screw is fastened to the receiving part.

18. The arrangement of claim 15, wherein the cap-shaped part comprises a manual actuating member.

19. The arrangement of claim 13, wherein the fastening screw has a disk-shaped head.

20. The arrangement of claim 13, wherein the engageable structure of the head comprises an actuating member configured to be engaged by a screwing tool for rotating the implant relative to the patient.

21. The arrangement of claim 20, wherein the actuating member comprises a polygonal part extending upwardly from the implant.

22. The arrangement of claim 13, wherein an angle between the longitudinal axis of the implant and the longitudinal axis of the fastening screw is between approximately 30° and 60°.

23. The arrangement of claim 22, wherein an angle between the longitudinal axis of the implant and the longitudinal axis of the fastening screw is approximately 45°.

24. The arrangement of claim 22, wherein the receiving part of the implant is located at an upper part of a first thread on the implant.

25. The arrangement of claim 22, wherein the end portion of the sleeve defines a planar surface configured to mate with the surface of the receiving part.

26. The arrangement of claim 13, wherein the head comprises a threaded aperture.

27. The arrangement of claim 13, wherein the planar surface of the receiving part traverses the longitudinal axis of the apical end of the implant.

28. The arrangement of claim 27, wherein the head comprises a threaded aperture that is coaxially aligned with the longitudinal axis of the implant.

29. The arrangement of claim 13, wherein the engageable structure of the head comprises at least one flat surface.

* * * * *